United States Patent [19]

Shu et al.

[11] 4,200,742
[45] Apr. 29, 1980

[54] CRYSTALLINE PURE 2,4,6-TRI-ISOBUTYL DIHYDRO-1,3,5-DITHIAZINE

[75] Inventors: Chi-Kuen Shu, Cliffwood; Braja D. Mookherjee, Holmdel; Manfred H. Vock, Locust, all of N.J.

[73] Assignee: International Flavors & Fragrances Inc., New York, N.Y.

[21] Appl. No.: 10,887

[22] Filed: Feb. 9, 1979

Related U.S. Application Data

[63] Continuation-in-part of Ser. No. 961,684, Nov. 17, 1978.

[51] Int. Cl.² .............................................. C07D 285/00
[52] U.S. Cl. .............................................. 544/5
[58] Field of Search ............................................ 544/5

[56] References Cited
U.S. PATENT DOCUMENTS 2,727,036  12/1955  McDermott ............................. 544/5
3,650,771  3/1972   Wiener et al. ........................... 544/5
3,966,988  6/1976   Wilson .................................. 544/5

Primary Examiner—John M. Ford
Attorney, Agent, or Firm—Arthur L. Liberman; Franklin D. Wolffe

[57] ABSTRACT

A small but effective amount of a pure crystalline or substantially pure compound represented by the formula:

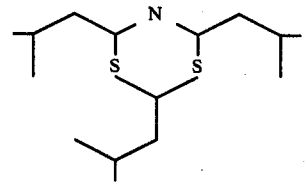

is used to alter, modify or enhance the flavor and aroma characteristics of a foodstuff having a bacon, caramel, roasted meat, roasted nut or fowl flavor and aroma.

1 Claim, 4 Drawing Figures

GLC PROFILE
EXAMPLE I

GLC PROFILE
EXAMPLE I

NMR SPECTRUM FOR EXAMPLES I & II

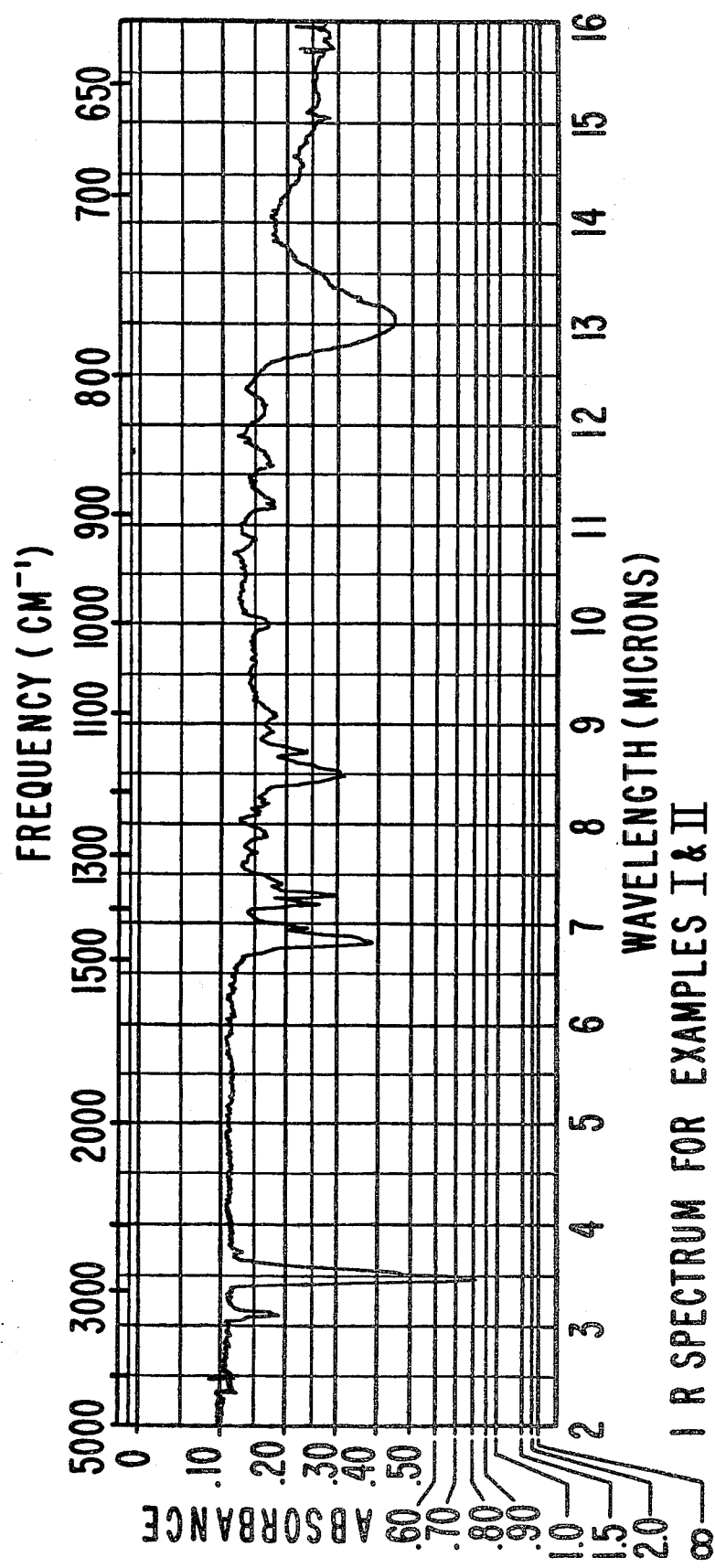

CRYSTALLINE PURE 2,4,6-TRI-ISOBUTYL DIHYDRO-1,3,5-DITHIAZINE

This application is a continuation-in-part of application for U.S. letters Pat., Ser. No. 961,684 filed on Nov. 17, 1978.

BACKGROUND OF THE INVENTION

This invention pertains to the use of a certain dithiazine to alter, modify or enhance the flavor and aroma of a foodstuff having a bacon or caramel or roasted meat or roasted nut or fowl flavor and aroma.

There is a continuing search for compositions which can vary, fortify, modify, enhance or otherwise improve (i.e., alter) the flavor and aroma of a foodstuff. To be fully satisfactory, such compositions should be stable, non-toxic and blendable with other ingredients to provide their own unique flavor and aroma nuance without detracting from the co-ingredients. Preferably, such compositions should be naturally occurring or present in natural foodstuffs (although unrecognized as flavor components thereof) so that their ingestible safety can be readily recognized. Additionally, these materials should be capable of being synthesized in a simple and economic manner.

Ingredients for foodstuff flavors having aromas and tastes which are compatible from an esthetic standpoint and from a chemical standpoint with meats and meat flavors are particularly desirable. More specifically, roasted, fried and fried bacon and caramel-like (with roasted and burnt nuances) aroma and flavor characteristics are particularly useful for bacon flavors and caramel flavors. In addition, they are useful for roasted meat, roasted nut and fowl (e.g., chicken and duck) foodstuff flavors and to augment and enhance such flavors.

U.S. Pat. No. 3,966,988 discloses the use of a small but effective amount of a compound represented by the formula:

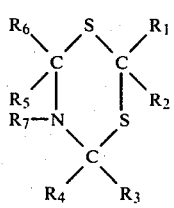

wherein $R_1$, $R_3$ and $R_5$ are the same and are lower alkyl of from 1 to 5 carbon atoms, $R_2$, $R_4$, and $R_6$ are hydrogen and $R_7$ is hydrogen or lower alkyl of from 1 to 5 carbon atoms; is used to alter, modify or enhance the flavor and aroma characteristics of foodstuffs, perfumes and perfumed articles. Specifically disclosed and exemplified is the compound 2,4,6-trimethyldihydro-1,3,5-dithiazine. This compound is also specifically characterized. In addition, however, the compound 2,4,6-tri-isobutyl-dihydro-1,3,5-dithiazine is disclosed but is not specifically characterized in said U.S. Pat. No. 3,966,988. Nor is the pure crystalline form of said 2,4,6-tri-isobutyldihydro-1,3,5-dithiazine disclosed therein.

A bacon flavor is indicated to be prepared according to U.S. Pat. No. 3,650,771 issued on Mar. 21, 1972. In said U.S. Pat. No. 3,650,771 the reaction product of 2-aminoethanol hydrosulfide and isovaleraldehyde is indicated to give a strong crisp bacon product when said 2-aminoethanol hydrosulfide and isovaleraldehyde are mixed together and heated over a temperature of 70°–80° C. for a period of about five minutes. It is noteworthy that the bacon flavor and aroma of the compound having the structure:

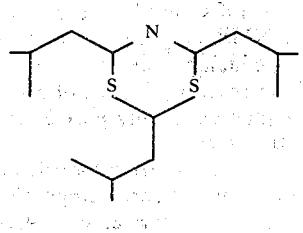

is surprisingly intense and longer lasting than is the bacon flavor and aroma of any of the reaction products of U.S. Pat. No. 3,650,771, particularly the reaction product of 2-aminoethanol hydrosulfide and isovaleraldehyde. On the other hand, the compound having the structure:

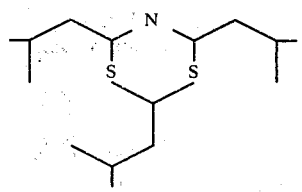

can be either (i) extracted by means of high pressure liquid chromatography or (ii) isolated by means of acidification followed by crystallization, neutralization and recrystallization from the reaction mixture resulting from the reaction of ammonium hydrosulfide with isovaleraldehyde or resulting from the reaction of the shiff base of ammonia and isovaleraldehyde with hydrogen sulfide or resulting from the reaction of ammonium sulfide with isovaleraldehyde in the presence of citric acid and water.

The compound having the structure:

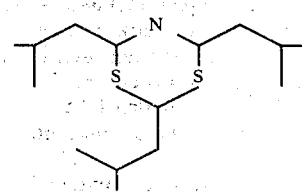

is specifically disclosed by Beilstein at Vol. I-V-27 (4) wherein it is indicated to have the common name "Valeraldin" and can be synthesized by reacting ammonia with thioisovaleraldehyde.

No mention is made in any of the prior art including the Beilstein reference and U.S. Pat. No. 3,966,988 issued on June 29, 1976 of the existence of pure crystalline or substantially pure 2,4,6-tri-isobutyl-dihydro-1,3,5-dithiazine or the use thereof as a bacon flavor ingredient or a caramel flavor ingredient for its enhancement, imparting or augmenting properties.

BRIEF DESCRIPTION OF THE DRAWINGS

FIG. 4 is the infrared spectrum for fractions 17 and 18 of the high pressure liquid chromatographic separation product of Example I, crystalline 2,4,6-tri-isobutyl-dihydro-1,3,5-dithiazine.

THE INVENTION

Figure 1:
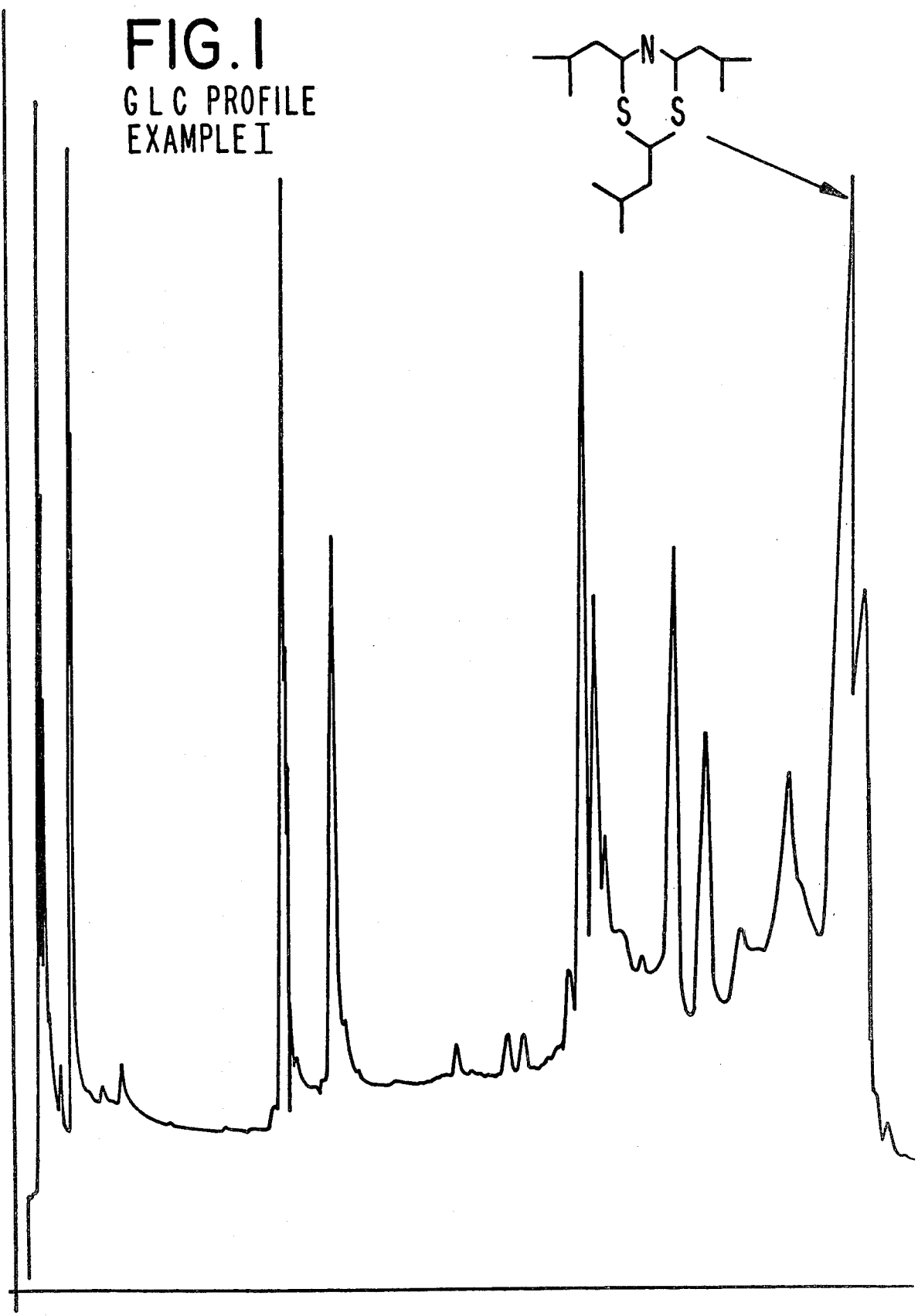
FIG. 1 is the GLC profile of the reaction product produced according to Example I wherein isovaleraldehyde and ammonia is reacted in the presence of hydrogen sulfide.

This invention has to do with the use of pure crystalline or substantially pure 2,4,6-tri-isobutyldihydro-1,3,5-dithiazine to alter, modify, enhance the flavor and aroma of a foodstuff having a bacon flavor or impart a bacon flavor to a foodstuff.

The pure crystalline or substantially pure 2,4,6-tri-isobutyl-dihydro-1,3,5-dithiazine of our invention has a structure:

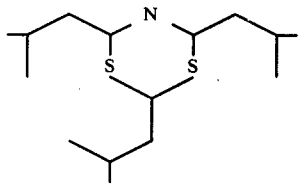

and has roasted, fried and fried bacon and aroma and flavor characteristics and in addition a roasted potato skin flavor characteristic causing it to be useful in roasted meat, roasted nut, bacon, caramel and fowl flavors. A physical form of 2,4,6-tri-isobutyl-dihydro-1,3,5-dithiazine, being in pure and crystalline or substantially pure form is novel per se. The process for preparing same is also novel in that, heretofore, (i) high pressure liquid chromatographic techniques and (ii) acidification, crystallization, neutralization and recrystallization techniques have never been used to obtain such a compound from a reaction product.

The 2,4,6-tri-isobutyl-dihydro-1,3,5-dithiazine of our invention in pure crystalline or substantially pure form is obtained by:

(A) First reacting isovaleraldehyde with ammonia to form a Shiff Base and reacting the resulting Shiff Base with hydrogen sulfide. The reaction of the isovaleraldehyde with ammonia takes place at a temperature of between −15° and 0° C. It is preferred that the mole ratio of ammonia:isovaleraldehyde is between 2:1 and 1:0.5 with a preferred mole ratio of 1:1.5. The resulting Shiff Base is then reacted with hydrogen sulfide at atmospheric pressure, preferably at room temperature over a period of time of between 1 and 5 hours, preferably 2–3 hours. Higher pressures may be used without detrimentally affecting the yield but no particular advantages are obtained in using pressures above one atmosphere.

The reaction product is then extracted with an inert organic solvent such as anhydrous diethyl ether, the extract is then dried over such materials as anhydrous sodium sulfate and the solvent is stripped off by such means as evaporation on a rotary evaporator. The resulting crude material is then microdistilled in order to get rid of low boiling fractions and the residue is subjected to column chromatography using such eluting materials as isopentane and/or diethyl ether in isopentane in various percentages of diethyl ether in isopentane such as 0.5% and 1%. The resulting fractions from the first column chromatographic separation are subjected to column chromatography a second time using for example a silica column using as eluting agents isopentane, 0.5% diethyl ether in isopentane, 1% diethyl ether in isopentane and 2% diethyl ether in isopentane. A product resulting from the second column chromatographic separation (combined fractions) are then subjected to high pressure liquid chromatography at a rate of between 100 and 500 ml per minute, preferably at about 350 ml per minute. The fractions are analyzed and selected for the purity of 2,4,6-tri-isobutyl-dihydro-1,3,5-dithiazine in said fractions. In one such Example, fractions 17 and 18 were selected yielding 100% 2,4,6-tri-isobutyl-dihydro-1,3,5-dithiazine in crystalline form after solvent evaporation.

(B) Reacting isovaleric aldehyde with ammonium sulfide in citric acid in aqueous media at a temperature of between 0° and 15° C. It is preferred that the mole ratio of ammonium sulfide:isovaleraldehyde is between 2:1 and 1:0.5 with a preferred mole ratio of 1:1.5. The reaction time is preferably between 1 and 5 hours. Higher pressures may be used without detrimentally affecting the yield but no particular advantages are obtained in using pressures above one atmosphere. The resulting reaction mass exists in the form of a "gel" and this "gel" is converted to a two (liquid phase) system—an organic phase and an aqueous phase. The organic phase is admixed with aqueous mineral acid, for example, 5% hydrochloric acid whereupon a crystalline precipitate is formed. The crystals are separated and washed with a non-dissolving hydrocarbon, such as hexanes and then neutralized by dissolving in a solvent, such as diethyl ether and treating with a weak base, such as 5% aqueous sodium carbonate. The excess base is then washed out and the organic solution is dried and evaporated yielding the pure or substantially pure 2,4,6-tri-isobutyl-dihydro-1,3,5-dithiazine in crystalline form.

The structural formula for 2,4,6-tri-isobutyl-dihydro-1,3,5-dithiazine given herein contemplated and includes cis and trans and other conformational isomers. When the 2,4,6-tri-isobutyl-dihydro-1,3,5-dithiazine in pure and crystalline or substantially pure form according to this invention is used in a flavoring composition, it can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious conventional materials can be used and broadly include other flavor materials, vehicles, stabilizers, thickeners, surface active agents, conditioners and flavor intensifiers.

The term "foodstuff" as used herein includes both solid and liquid ingestible materials for man or animals which materials usually do, but need not, have nutritional value. Thus, foodstuffs include meats, gravies, soups, convenience foods, malt and other alcoholic or non-alcoholic beverages, nut butters such as peanut butter and other spreads, seafoods including fish, crustaceans, mollusks and the like, candies, breakfast foods, baked goods, vegetables, cereals, soft drinks, snack foods, pet foods such as dog and cat foods, other veterinary products, and the like.

The terms "alter" and "modify" (in their application to foodstuffs) in its various forms will be understood herein to mean the supplying or imparting of a flavor character to note to an otherwise bland, relatively tasteless substance, or augmenting and existing flavor characteristic where the natural flavor is deficient in some regard, or supplementing the existing flavor impression to modify the organoleptic character.

The term "enhance" is used herein to mean the intensification of a flavor or aroma characteristic or note without the modification of the quality thereof. Thus, "enhancement" of a flavor or aroma means that the enhancement agent does not add any additional flavor note.

Conventional flavoring materials as indicated above include saturated and unsaturated fatty and amino acids, alcohols, including primary and secondary alcohols; esters, carbonyl compounds including ketones and aldehydes; lactones, other cyclic organic materials including benzene derivatives, alicyclics, hetero-cyclics such as furans, pyridines, pyrazines and the like; sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla and caramel; essential oils and extracts such as anise oil, clove oil and the like; artificial flavoring materials such as vanillin; and the like. Particularly useful flavoring agents and adjuvants are cyclopentane thiol, protein hydrolysate, such as hydrolyzed vegetable protein, cysteine, salts of cysteine such as cysteine hydrochloride, thiamine, salts of thiamine, 2,5-dimethyl-3-hydroxy-4-oxo-4,5-dihydrofuran, and products resulting from heating a mixture of at least two differing materials of the foregoing and high pressure (2–10 atmospheres) reaction products of $H_2S$ and 2,5-dimethyl-3-hydroxy-4-oxo-4,5-dehydrofuran, heliotropin, cyclotene, ethyl cyclotene, maltol, ethyl maltol, 6-methyl coumarin, vanillin, ethyl vanillin, levulinic acid, isovaleraldehyde, furfural, rum ether, ethyl levulinate and peruvic acid.

Stabilizers include preservatives such as sodium chloride, and the like; antioxidants such as calcium and sodium ascorbate, ascorbic acid, butylated hydroxyanisole, butylated hydroxytoluene, propyl gallate and the like; sequestrants such as citric acid, EDTA, phosphates, and the like.

Thickeners include carriers, binders, protective colloids, suspending agents, emulsifiers and the like, such as agar-agar, carrageenan, cellulose and cellulose derivatives such as carboxymethyl cellulose and methyl cellulose, natural and synthetic gums such as gum arabic, gum tragacanth and the like, and other proteinaceous materials, lipids, carbohydrates, starches and pectins.

Surface active agents include emulsifying agents such as mono-and/or diglycerides of fatty acids such as caproic acid, caprylic acid, palmitic acid, myristic acid, oleic acid, and the like; lecithin; defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite, propylene oxide, succinic anhydride and the like; buffers and neutralizing agents such as sodium acetate, sodium diacid phosphate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anti-caking agents such as aluminum calcium sulfate and tribasic calcium phosphate; enzymes, yeast foods such as calcium lactate and calcium sulfate; nutrient supplements such as iron salts, such as ferric phosphate, ferric pyrophosphate, ferrous gluconate and the like, riboflavin, vitamins; zinc sources such as zinc chloride, zinc sulfate and the like.

The 2,4,6-tri-isobutyl-dihydro-1,3,5-dithiazine in pure crystalline or substantially pure form, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The 2,4,6-tri-isobutyl-dihydro-1,3,5-dithiazine in pure crystalline or substantially pure form can be incorporated with the carriers by conventional means such as spray-drying drum drying, and the like. Such carriers can also include materials for coacervating the 2,4,6-tri-isobutyl-dihydro-1,3,5-dithiazine in pure crystalline or substantially pure form (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

It will be understood by those skilled in the art that the 2,4,6-tri-isobutyl-dihydro-1,3,5-dithiazine in pure crystalline or substantially pure form can be added to the materials to be flavored at any convenient point in the production of the finished product. Thus, when they are used to alter or otherwise vary the flavor of a foodstuff, they can be added in the original mixture, dough, emulsion, batter or the like, prior to any cooking or heating operation. Alternatively, they can be added at a later state of processing if volatilization losses would be excessive during the earlier processing.

The quantity of 2,4,6-tri-isobutyl-dihydro-1,3,5-dithiazine in pure crystalline or substantially pure form or mixtures thereof utilized should be sufficient to impart the desired flavor characteristic to the product, but on the other hand, the use of an excessive amount of the 2,4,6-tri-isobutyl-dihydro-1,3,5-dithiazine in pure crystalline or substantially pure form is not only wasteful and uneconomical but in some instances too large a quantity may unbalance the flavor or other organoleptic property of the product to be consumed. The quantity used will vary depending upon the ultimate foodstuff or other consumable product; the amount and type of flavor initially present in the product; the further process or treatment steps to which the product will be subjected; regional and other preference factors; the types of storage, if any, to which the product will be subjected; and the preconsumption treatment, such as baking, frying, and so on, given to the product by the ultimate consumer.

It is accordingly preferred that the ultimate compositions contain from about 0.002 parts per million (ppm) to about 100 ppm of the 2,4,6-tri-isobutyl-dihydro-1,3,5-dithiazine in pure crystalline or substantially pure form. More particularly, in food compositions it is desirable to use from about 0.02 to about 20 ppm and in certain preferred embodiments of the invention, from about 0.1 to about 15 ppm of the 2,4,6-tri-isobutyl-dihydro-1,3,5-dithiazine in pure crystalline or substantially pure form are included in the finished product.

The amount of 2,4,6-tri-isobutyl-dihydro-1,3,5-dithiazine in pure crystalline or substantially pure form to be utilized in flavoring or flavor-enhancing compositions can be varied over a wide range depending upon a particular quality to be added to the foodstuff, tobacco, or other consumable material. Thus, amounts of one or more 2,4,6-tri-isobutyl-dihydro-1,3,5-dithiazine in pure crystalline or substantially pure form according to the present invention from about 0.02 up to 80 or 90% can be incorporated in such compositions. It is generally found to be desirable to include from about 0.02 to about 25% of the 2,4,6-tri-isobutyl-dihydro-1,3,5-dithiazine in pure crystalline or substantially pure form in such compositions.

The following examples are given to illustrate embodiments of the invention as it is presently preferred to practice it. It will be understood that these examples are illustrative, and the invention is not to be considered as restricted thereto except as indicated in the appended claims.

All parts, proportions, percentages, and ratios herein are by weight unless otherwise indicated.

EXAMPLE I

PREPARATION OF PURE CRYSTALLING OR SUBSTANTIALLY PURE 2,4,6-TRI-ISOBUTYL-DIHYDRO-1,3,5-DITHIAZINE

Reaction:

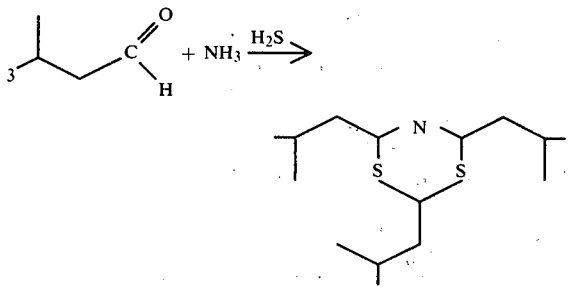

Into a 1 liter, 3-neck flask equipped with mechanical stirrer, additional funnel, thermometer and condenser is placed 350 grams of 30% aqueous ammonia with stirring at $-9°$ C. 172 Grams of isovaleraldehyde is added dropwise over a 45 minute period while maintaining the reaction temperature at between $-10°$ C. and $0°$ C.

The addition funnel is then removed and the solids on the inside glass wall of the flask are washed with 150 ml water. The flask is then stoppered. The reaction mass is then allowed to come to room temperature with stirring over a period of 130 minutes.

The flask is unstopped and hydrogen sulfide gas is bubbled into the reaction mass over a period of 1 hour and 45 minutes via a gas dispersion tube.

Three hundred ml volumes of diethyl ether is then used to extract the organic layer. The ether layer is then washed with saturated sodium chloride-water until neutral and dried over anhydrous sodium sulfate. The solvent is then removed by means of a rotary evaporator and 150 grams crude material is obtained.

A sample of the crude material is trapped out using GLC trapping (conditions: SE 30 stainless steel $10' \times \frac{1}{8}''$ column programmed at $65°-210°$ C. at $6°$ C. per minute.

GLC profile is set forth in FIG. 1.

In order to remove the "lights" the material is microdistilled under 0.5 mm Hg pressure. The distillation is continued and the temperature in the distillation flask reaches $120°$ C. The residue in the distillation flask is removed and subjected to column chromatography on a 5% $H_2O$ deactivated $SiO_2$ column (850 grams). Thus, 35 grams of crude material from the distillation flask is placed on the column using the following solvents:

a. 4 liters isopentane
b. 4 liters 0.5% diethyl ether in isopentane
c. 8 liters 1% diethyl ether in isopentane The fractions are monitored using thin layer chromatography and gas chromatography. The combined fractions indicate 90% purity on GLC. The combined fractions weights about 10 grams.

The resulting combined material is again subjected to a second column chromatographic separation using undeactivated $SiO_2$, 200 grams. 9 Grams of the first combined column chromatography-separated material is subjected to the column and the solvents used are as follows:

a. 1 liter isopentane
b. 0.6 liters 0.5% diethyl ether in isopentane
c. 1.5 liters 1% diethyl ether in isopentane
d. 1.5 liters 2% diethyl ether in isopentane The fractions are combined and indicate 92% pureity. The weight of the resulting material is 8.5 grams.

Figure 2:
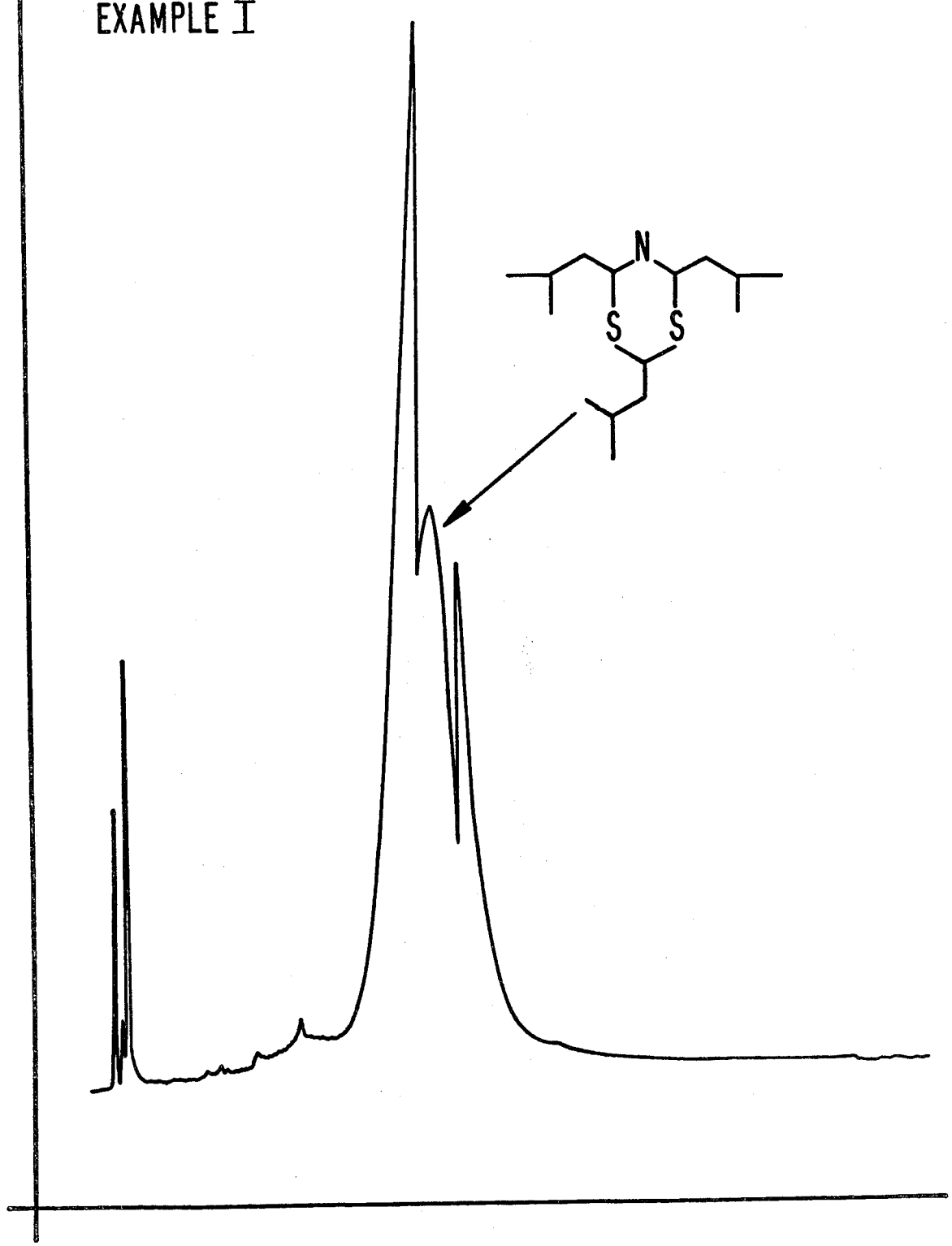
FIG. 2 is the GLC profile of the reaction product produced according to Example I, purified by high pressure liquid chromatography (GLC conditions: Carbowax 20 m column; stainless steel 10'×⅛" programmed at 65°–210° C. at 15° C. per minute.

About 4 grams of this material obtained from the second column chromatographic separation is injected on a "Ater's" preparatory "500" high pressure liquid chromatography column. The fractions collected are monitored by thin layer chromatography. The "best" fractions observed on thin layer chromatography indicate 98% purity on GC. The high pressure liquid chromatography GC profile is set forth in FIG. 2.

The high pressure liquid chromatography conditions are:

350 ml/minute: one $SiO_2$ column chart speed 0.5 inches per minute.

The material obtained from high pressure liquid chromatography is about 2.3 grams. Fractions 17 and 18 are combined. The fractions 17 and 18 are 100% 2,4,6-tri-isobutyl-dihydro-1,3,5-dithiazine having the structure:

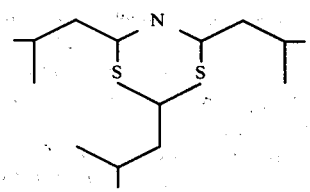

Figure 3:
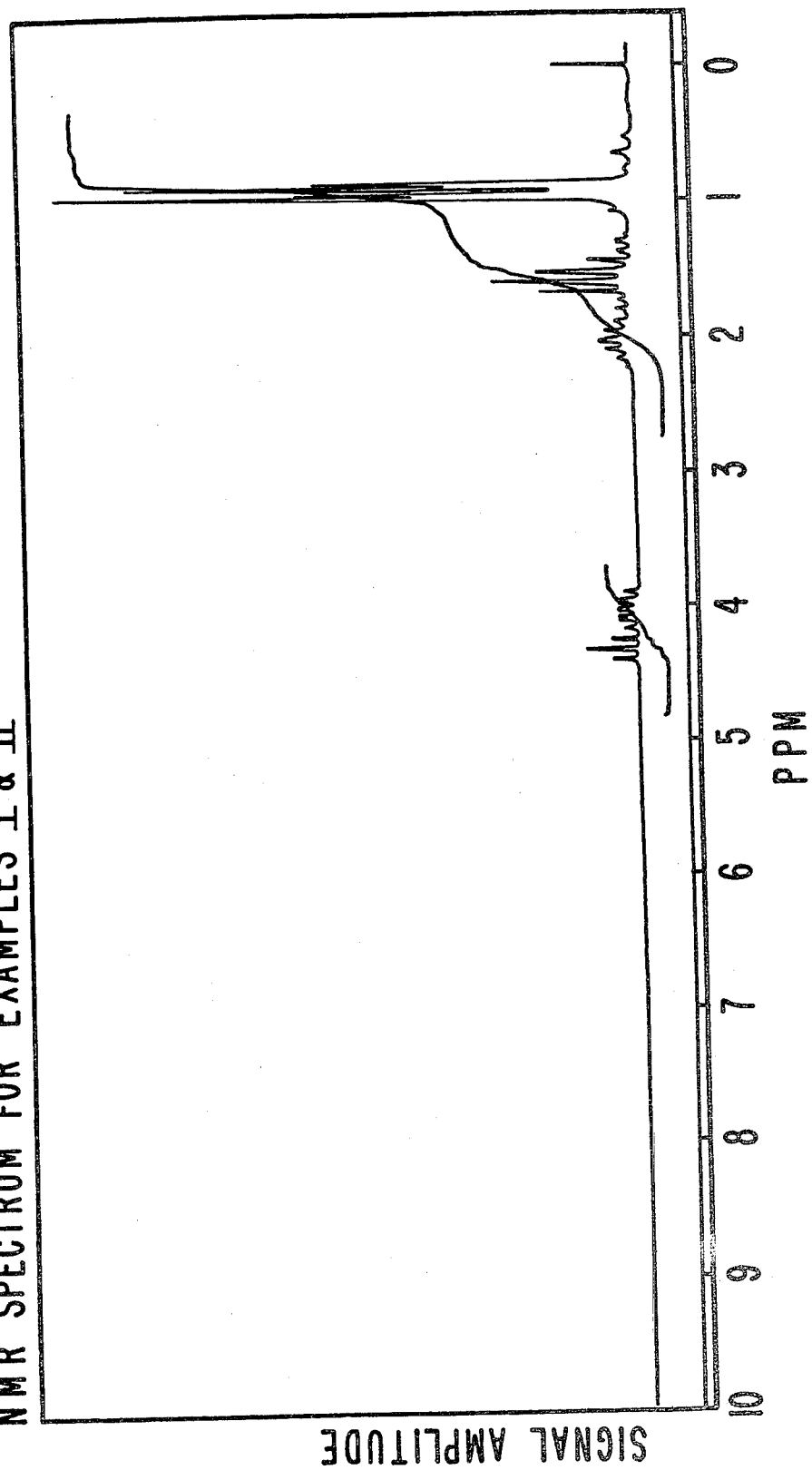
FIG. 3 is the NMR spectrum for fractions 17 and 18 resulting from the high pressure liquid chromatography separation of the reaction product of Example I. It is pure crystalline or substantially pure 2,4,6-tri-isobutyl-dihydro-1,3,5-dithiazine.

The NMR spectrum for fractions 17 and 18 of the high pressure liquid chromatography separation is set forth in FIG. 3. The IR analysis for fractions 17 and 18 resulting from the high pressure liquid chromatography separation is set forth in FIG. 4.

The GC conditions for the GC profile of the high pressure liquid chromatography separation product are:

Carbowax 20 m column: stainless steel 10'×⅛" programmed at 65°–210° C. at 15° C. per minute.

The Mass Spectral analysis for the 2,4,6-tri-isobutyl-dihydro-1,3,5-dithiazine, crystallized and purified of fractions 17 and 18 is as follows:

| M/E | Relative Intensity |
| --- | --- |
| 39 | 29 |
| 41 | 79² |
| 43 | 100¹ |
| 45 | 37⁶ |
| 58 | 36 |
| 60 | 40⁵ |
| 69 | 50⁴ |
| 87 | 35 |
| 96 | 30 |
| 102 | 54³ |
| M289 | 5 |

EXAMPLE II

The following ingredients are homogeneously admixed at 25° C:

| Ingredients | Parts |
| --- | --- |
| Vegetable Shortening | 622.7 |
| Salt | 321.7 |
| Glutamic Acid | 5.1 |
| L-Cysteine Hydrochloride | 10.3 |
| Glycine | 5.1 |
| β-Alanine | 1.3 |
| Taurine | 20.0 |
| Mixture of di-sodium inosinate and di-sodium guranylate | 3.3 |

The mixture is heated to 300° F. for 30 seconds. After cooling to 100° F., 0.05 parts of 2,4,6-tri-isobutyl-dihydro-1,3,5-dithiazine, crystallized and purified or substantially purified produced according to Example I are added.

The resulting mixture has an excellent bacon aroma and taste.

EXAMPLE III

Cysteine hydrochloride in the amount of 8.8 g is refluxed at 215° F. under atmospheric pressure for four hours with a mixture of 309 g of hydrolyzed vegetable protein and 674 g of water. Subsequent to the reflux, the mixture is cooled and 0.05 g of 2,4,6-tri-isobutyl-dihydro-1,3,5-dithiazine, crystallized and purified or substantially purified produced according to Example I is added and intimately admixed with the composition. The mixture has an excellent fried bacon flavor of high intensity.

EXAMPLE IV

The composition prepared in Example II is dissolved in propylene glycol to provide a 0.1% solution. This solution in the amount of 0.966 g is added to 7.3 g of a soup base consisting of:

| Ingredients | Parts |
| --- | --- |
| Fine ground sodium chloride | 35.62 |
| Hydrolyzed vegetable protein | 27.40 |
| Monosodium glutamate | 17.81 |
| Sucrose | 10.96 |
| Beef fat | 5.48 |
| Sethness caramel color (powder B & C) | 2.73 |

The resulting mixture is added to 12 ounces of boiling water to obtain a soup having an excellent bacon flavor.

EXAMPLE V

The composition prepared in Example III is dissolved in propylene glycol to provide a 0.1% solution. This solution in the amount of 0.966 g is added to 7.3 g of a soup base consisting of:

| Ingredients | Parts |
| --- | --- |
| Fine ground sodium chloride | 35.62 |
| Hydrolyzed vegetable protein (Maggi 4BE) | 27.40 |
| Monosodium glutamate | 17.81 |
| Sucrose | 10.96 |
| Beef fat | 5.48 |
| Caramel color, bakers and confectioner's powder grade | 2.73 |

The resulting mixture is added to 12 ounces of boiling water to obtain a soup having an excellent bacon flavor.

EXAMPLE VI

One-half gram of the soup base mixture of Example IV is emulsified in a solution containing 100 g gum arabic and 300 g water. The emulsion is spray-dried with a Bowen Lab Model Drier utilizing 250 cfm of air with an inlet temperature of 500° F., an outlet temperature of 200° F., and a wheel speed of 50,000 rpm.

Twelve grams of the spray-dried material is mixed with 29.2 g of the soup base set forth in Example IV. The resulting mixture is then added to 12 ounces of boiling water and an excellent bacon flavored soup is obtained.

EXAMPLE VII

LARGE SCALE PREPARATION OF CRYSTALLINE 2,4,6-TRI-ISOBUTYL-DIHYDRO-1,3,5-DITHIAZINE

Reaction:

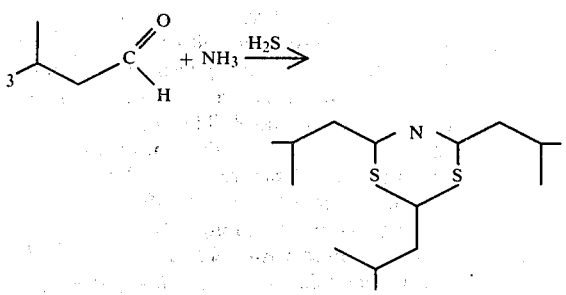

To a 22 liter reaction flask equipped with air stirrer, cooling bath, thermometer, addition funnel, reflux condenser and gas outlet and bubbler, dry trap, 30% caustic trap and nitrogen inlet, 6,480 grams of distilled water is added followed by 4,146 grams of citric acid. The flask is then packed with wet ice and cooled to 10° C. 1,395 Grams of isovaleric aldehyde is added to the reaction mixture which is again cooled to 10° C. Over a period of 1 hour, 2,502 grams of 22% ammonium sulfide is added to the reaction mass while maintaining it at a temperature in the range of 10°–18° C. and applying a nitrogen sweep to the head space in the reaction flask. The reaction mass is then stirred for a period of 10 hours whereby the gel formed therein is converted to oil.

The reaction mass is poured into a 10 gallon open head funnel and the flask is rinsed with 1 liter of diethyl ether. The ether washings are also poured into the open head separatory funnel. The contents of the separatory funnel is stirred slowly for a period of 3 minutes and then permitted to separate into two liquid phases. The upper organic layer is removed and the lower aqueous layer is extracted with two 1 liter volumes of diethyl ether. The organic phase and the ether extracts are combined with the reaction product resulting from a second run identical to the first run above.

Into a 12 liter separatory funnel the filtered organic layers from the two runs are added together with 2 liters of a 5% hydrochloric acid solution. The contents of the separatory funnel are stirred and permitted to separate. A white salt forms. The aqueous layer is removed and discarded and the solids are filtered from the organic layer. The crystals are washed with portions of diethyl ether totaling 600 ml yielding 920 grams of salt. To the filtrate, 1.4 liters of 5% hydrochloric acid solution is added with stirring. More white crystals are formed and permitted to separate. The lower aqueous layer is discarded and the organic layer is filtered and the crystals are washed with anotheer 600 ml of diethyl ether. To the filtrate, another 1.4 liters of 5% hydrochloric acid solution is added with stirring and a smaller amount of white crystals is formed and permitted to separate. Again, the lower aqueous layer is discarded. The upper organic layer is filtered and the crystals are washed with 600 ml ether. All crystal batches are combined for washing (1025 grams wet weight).

The resulting combined solids are slurried in a 5 liter flask with 3,000 ml hexane. The material is then filtered and the filter cake is rinsed with portions of hexane totaling about 1.5 liters. GLC analysis at this point indicates all trimer of isovaleric aldehyde (by product) is eliminated.

The solids are added to a 20 liter separatory funnel followed by 6 liters of diethyl ether and 5 liters of a 5% aqueous sodium carbonate solution. The contents of the separatory funnel are then stirred vigorously until they dissolve. The upper ether layer is removed and the lower aqueous layer is extracted with two 1 liter volumes of diethyl ether. The organic phases are combined and washed with 1 liter of saturated sodium chloride until the pH is between 6 and 7. The organic layer is then dried over 260 grams of anhydrous magnesium sulfate. The resulting dried material is distilled using a 3 liter distillation flask and a "continuous feed rush over apparatus". The product remaining in the distillation flask is filtered and rinsed with cold diethyl ether (400 ml). The resulting crystals are dried yielding 160 grams of product. Recrystallizations are carried out from the mother liquor yielding a total of 450 grams of the product.

GLC, NMR and IR analyses yield the information that this product is substantially pure 2,4,6-tri-isobutyl-dihydro-1,3,5-dithiazine having the structure:

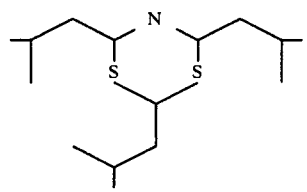

EXAMPLE VIII

BASIC BACON FLAVOR FORMULATION

The following basic bacon flavor formulation is prepared:

| Ingredients | Parts by Weight |
|---|---|
| Vanillin | 2.0 |
| Eugenol | 1.0 |
| Guaicol | 0.2 |
| Para-vinyl guaicol | 0.2 |
| Cyclotene | 1.0 |
| Trimethyl pyrazine | 0.4 |
| Acetyl pyridine | 0.1 |
| 2,4-Decadienal (1% in food grade ethanol) | 0.1 |
| Furfural | 0.4 |
| Benzaldehyde | 1.0 |
| Isovaleraldehyde | 1.0 |
| Methyl thiazole alcohol | 7.6 |
| Food grade Ethanol | 185.0 |
| Hickory Smoke Flavor (obtained from Fleischmann Distilling Corporation, Inc., 625 Madison Avenue, New York, New York) | 800.0 |

The above formulation is divided into parts. To the first part, nothing is added. To a second part at the rate of 0.02 ppm, the 2,4,6-tri-isobutyl-dihydro-1,3,5-dithiazine produced according to Example VII is added. Both basic bacon flavor formulations with and without the dithiazine prepared according to Example VII are compared at the rate of 100 ppm and evaluated by a flavorist expert panel. The flavor with the 2,4,6-tri-isobutyl-dihydro-1,3,5-dithiazine produced according to Example VII has a crisp bacon aroma and taste and additional pork fat notes not present in the basic bacon flavor. Therefore, the flavor with the 2,4,6-tri-isobutyl-dihydro-1,3,5-dithiazine is preferred by the panel.

EXAMPLE IX

BASIC CARAMEL FLAVOR FORMULATION

The following basic caramel flavor formulation is prepared:

| Ingredients | Parts by Weight |
|---|---|
| Heliotropine | 1.0 |
| Cyclotene | 2.0 |
| Maltol | 3.0 |
| 6-Methyl-coumarin | 3.0 |
| Vanillin | 4.0 |
| Ethyl vanillin | 3.0 |
| Levulinic acid | 8.0 |
| Isovaleraldehyde | 0.5 |
| Furfural | 0.1 |
| Rum Ether | 20.0 |

| Ingredients | Parts by Weight |
| --- | --- |
| Ethyl Levulinate | 0.9 |
| Pyruvic Acid | 15.0 |

This basic caramel flavor formulation is divided into two portions. To the first portion, nothing is added. To the second portion at the rate of 0.01 ppm, 2,4,6-tri-isobuyl-dihydro-1,3,5-dithiazine prepared according to Example VII is added. The flavor with and without said 2,4,6-tri-isobutyl-dihydro-1,3,5-dithiazine are compared at the rate of 10 ppm in water by a flavorist panel. The flavor with the 2,4,6-tri-isobutyl-dihydro-1,3,5-dithiazine has a very characteristic roasted and burnt character in both aroma and taste; not nearly as much as exists in the flavor without said dithiazine. Therefore, the flavor with the additional note is preferred by the bench panel of flavorists.

What is claimed is:

1. Pure crystalline 2,4,6-tri-isobutyl-dihydro-1,3,5-dithiazine having the structure:

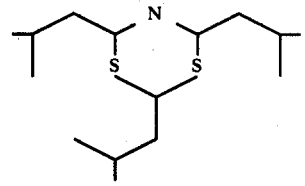

* * * * *